United States Patent [19]

Eiglmeier et al.

[11] Patent Number: 4,824,892

[45] Date of Patent: Apr. 25, 1989

[54] UV LIGHT STABILIZER BASED ON BENZOPHENONE

[75] Inventors: Kurt Eiglmeier, Neustadt; Joachim Schulz, Pohle, both of Fed. Rep. of Germany

[73] Assignee: Riedel-de Haen Aktiengesellschaft, Seelze, Fed. Rep. of Germany

[21] Appl. No.: 132,374

[22] Filed: Dec. 15, 1987

Related U.S. Application Data

[63] Continuation of Ser. No. 943,835, Dec. 18, 1986, abandoned, which is a continuation of Ser. No. 787,986, Oct. 16, 1985, abandoned.

[30] Foreign Application Priority Data

Oct. 18, 1984 [DE] Fed. Rep. of Germany ....... 3438190

[51] Int. Cl.$^4$ .................... C08K 5/13; C07C 69/734; C08F 120/30
[52] U.S. Cl. ................... 524/291; 252/407; 560/221; 560/8; 526/313; 558/400
[58] Field of Search .............. 524/291; 560/221, 8; 526/313; 252/407; 558/400

[56] References Cited

U.S. PATENT DOCUMENTS

| | | | |
|---|---|---|---|
| 3,291,837 | 12/1966 | Goldberg et al. | 560/221 |
| 3,341,493 | 9/1967 | Goldberg et al. | 560/221 |
| 3,365,421 | 1/1968 | Horton et al. | 560/221 |
| 3,580,927 | 5/1971 | Wear | 568/333 |
| 3,676,471 | 7/1972 | Eggensperger et al. | 524/291 |

OTHER PUBLICATIONS

Carlson et al: CA 62 11975h (1965).
Biryu Kov et al: CA 92 129819c (1980).
Toyobu Co Ltd: CA 98 127362y (1983).

*Primary Examiner*—Veronica P. Hoke
*Attorney, Agent, or Firm*—Curtis, Morris & Safford

[57] ABSTRACT

Benzophenone derivatives having at least one hydroxyl group in the ortho-position relative to the carbonyl group are used for stabilizing numerous substrates against the action of UV light. 1,3-bis-(4-Benzoyl-3-hydroxyphenoxy)-2-propanol is a photo-absorber containing two benzophenone groups. Particularly suitable stabilizers are esters of this substituted propanol with unsaturated carboxylic acids, for example esters of acrylic acid and methacrylic acid. These compounds are prepared by esterifying the substituted propanol with an unsaturated acid or by esterifying the substituted propanol with a saturated acid containing a reactive methylene group and subjecting the product to subsequent condensation with a keto compound. They can be polymerized and are suitable for the preparation of homopolymers and copolymers.

7 Claims, No Drawings

UV LIGHT STABILIZER BASED ON BENZOPHENONE

This application is a continuation of application Ser. No. 943,835, filed Dec. 18, 1986, now abandoned, which is a continuation of Ser. No. 787,986, filed Oct. 16, 1985, now abandoned.

The invention relates to esters of unsaturated carboxylic acids with an alcohol containing benzophenone groups, a process for the preparation thereof and the use of these esters as stabilizers against the effect of UV light.

It is known that 1,3-bis-(4-benzoyl-3-hydroxyphenoxy)-2-propanol acts as a photostabilizer for polymers (cf. Chem. Abstracts 86 (1977), 106,170 f). However, the effectiveness of this stabilizer still leaves something to be desired (cf. Chem. Abstracts 92 (1980), 129,819 c). It is also known that glycidyl (meth)acrylate forms an adduct with a polyhydroxybenzophenone which can be copolymerized with ethyl acrylate and methyl methacrylate (cf. Chem. Abstracts 98 (1983), 127,362 y). This copolymer is employed for coating polyester sheeting.

The object of the invention is to provide compounds which contain at least two benzophenone groups and one double bond in the molecule and which absorb UV light.

The invention relates to an ester formed from 1,3-bis-(4-benzoyl-3-hydroxyphenoxy)-2-propanol and an unsaturated carboxylic acid.

The invention also relates to a process for the preparation of an ester formed from a substituted propan-2-ol and an unsaturated carboxylic acid, which comprises (a) reacting 1,3-bis-(4-benzoyl-3-hydroxyphenoxy)-2-propanol with an unsaturated carboxylic acid in an inert organic solvent, in the presence of an acid catalyst, at a temperature of 0° to 150° C., or (b) first reacting 1,3-bis-(4-benzoyl-3-hydroxyphenoxy)-2-propanol—if appropriate in an inert organic solvent—in the presence of an acid catalyst, at a temperature of 0° to 150° C., with a saturated carboxylic acid containing an active methylene group, and then subjecting the resulting saturated ester to a condensation reaction with a keto compound in the presence of a catalyst.

The invention also relates to a stabilizer against the effects of UV light, which contains, as the active compound, an ester formed from 1,3-bis-(4-benzoyl-3-hydroxyphenoxy)-2-propanol and an unsaturated carboxylic acid. The invention also relates to the use of such an ester for stabilizing a plastic against the effects of UV light.

The 1,3-bis-(4-benzoyl-3-hydroxyphenoxy)-2-propanol ester according to the invention is, in particular, a compound of the formula (1)

having 1 to 8, preferably 1 to 4, carbon atoms or a phenyl radical which is optionally substituted by a lower alkyl or alkoxy radical which preferably contains 1 to 4 carbon atoms, or together denote an alkylene radical having 4 or 5 carbon atoms.

Finally, the invention also relates to a polymer composed of or containing recurring units derived from an ester formed from 1,3-bis-(4-benzoyl-3-hydroxyphenoxy)-2-propanol and an unsaturated carboxylic acid; the carboxylic acid is, in particular, a compound of the formula (2)

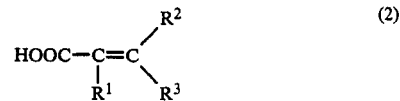

in which $R^1$ denotes a hydrogen atom, a phenyl radical, an alkyl radical having 1 to 12, preferably 1 to 4, carbon atoms or a cyano group and $R^2$ and $R^3$ independently of one another denote a hydrogen atom, an alkyl radical having 1 to 8, preferably 1 to 4 carbon atoms or a phenyl radical which can be substituted by a lower alkyl or alkoxy radical which preferably has 1 to 4 carbon atoms, or together denote an alkylene radical having 4 or 5 carbon atoms. Compounds of the formula (2) are, in particular, acrylic acid and substituted acrylic acids, for example methacrylic acid, crotonic acid, 2,2-diphenylacrylic acid, 2,2-dimethylacrylic acid and 1-cyanoacrylic acid.

The preparation of the ester according to the invention is effected in a one-stage process (variant a) or in a two-stage process (variant b); the reactions with the particular acid are carried out in an inert organic solvent, in the presence of an acid catalyst and at a temperature of 0° to 150° C., preferably 50° to 120° C.

The one-stage process comprises an esterification of 1,3-bis-(4-benzoyl-3-hydroxyphenoxy)-2-propanol with an unsaturated carboxylic acid, preferably an unsaturated monocarboxylic acid. A compound of the formula (2) is particularly suitable as the carboxylic acid. The carboxylic acid is employed in an excess of up to 10 moles per mole of propanol, preferably in an amount of 3 to 8 moles per mole of propanol.

The two-stage process comprises an esterification of 1,3-bis-(4-benzoyl-3-hydroxyphenoxy)-2-propanol with a saturated carboxylic acid, preferably a monocarboxylic acid, containing an active methylene group, and a subsequent condensation reaction of the resulting saturated ester with a keto compound. The saturated carboxylic acid used in this case is, in particular, cyanoacetic acid. Suitable keto compounds are symmetrical or asymmetrical aliphatic ketones, cyclic aliphatic ketones, aromatic ketones and aliphatic-aromatic ketones and also aliphatic and aromatic aldehydes. Examples of

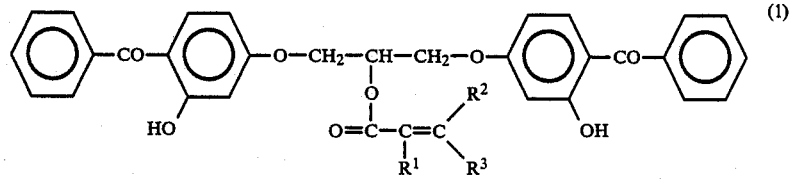

in which $R^1$ denotes a hydrogen atom, a phenyl radical, an alkyl radical having 1 to 12, preferably 1 to 4, carbon atoms or a cyano group and $R^2$ and $R^3$ independently of one another denote a hydrogen atom, an alkyl radical these are acetone, benzophenone, cyclohexanone, methyl ethyl ketone, formaldehyde and benzaldehyde.

The carboxylic acid and the keto compound are in each case employed in a molar excess, specifically an excess of up to 10 moles per mole of reactant, and preferably in an amount of 3 to 8 moles per mole of reactant.

The inert organic solvent is an aromatic hydrocarbon which contains 6 to 8 carbon atoms and which can be substituted by a halogen atom, preferably a chlorine atom, or is an aliphatic halogenated hydrocarbon, preferably a chlorinated hydrocarbon having 1 to 2 carbon atoms. Examples of suitable solvents are benzene, toluene, xylene, chlorobenzene, chloroform, carbon tetrachloride and 1,2-dichloroethane. The solvent is used in an amount of 1 to 10 liters per mole of substituted propanol; an amount of 5 to 8 liters/mole is preferred. The use of an inert organic solvent is not necessary when carrying out the two-stage process, if a liquid keto compound is used.

The catalyst used for the esterification reaction is an acid catalyst, i.e. an inorganic acid or an organic acid or, in particular, an organic sulfonic acid which can contain halogen atoms, preferably fluorine atoms; an acid ion exchanger is also suitable. Examples of suitable catalysts are p-toluenesulfonic acid and, above all, trifluoromethanesulfonic acid. The catalyst is employed in an amount of 1 to 10, preferably 3 or 6, percent by weight (relative to the substituted propanol). The same catalyst can be used for the condensation reaction. However, a basic catalyst is also suitable, i.e. an alkali metal acetate, such as sodium acetate and potassium acetate, and also ammonium acetate. The basic catalyst is optionally employed in an amount of 5 to 20, preferably 10 to 15, percent by weight (relative to the saturated ester).

The compounds according to the invention are crystalline substances which are obtained in a good yield and in a high state of purity. (The degree of purity is determined by high-pressure liquid chromatography—HPLC). They are suitable for use as stabilizers for protecting plastics, for example polyacrylic acid esters, polymethacrylic acid esters, polystyrene and ABS polymers, against the action of ultraviolet light. When plastics articles are produced by thermoplastic shaping, the stabilizers can be incorporated into the plastic composition so that light stabilization is achieved in the composition and not only on the surface of the article. The compounds are distinguished by having a low vapor pressure and a low tendency to migration.

The compounds according to the invention can be polymerized and are suitable for use as monomers for the preparation of homopolymers and copolymers, especially in the polymerization of individual vinyl compounds or mixtures of vinyl compounds, for example acrylic acid ester, methacrylic acid esters, acrylonitrile, styrene and α-methylstyrene. Depending on the reaction conditions in the homopolymerization, they form soft to glass-like polymers which are suitable for use, for example, as coating agents. The invention is illustrated in greater detail by the examples which follow. Percentage data relate in each case to weight. UV spectra were determined in each case by means of a commercially available spectrophotometer. In the examples, the concentration of the substance to be investigated was 0.001 percent by weight, the solvent used was dimethylformamide and the determination was carried out at a layer thickness of 1 cm.

EXAMPLE 1

3 g of trifluoromethanesulfonic acid, 0.1 g of hydroquinone and 0.1 g of hydroquinone monomethyl ether were added to a solution of 48.5 g (0.1 mole) of 1,3-bis-(4-benzoyl-3-hydroxyphenoxy)-2-propanol and 43.6 g (0.6 mole) of acrylic acid in 600 ml of toluene, and the solution was heated for 3 hours at a temperature of 105° to 110° C. After cooling to room temperature, the reaction mixture was washed with 1.5 liters of water. The toluene was then distilled off from the reaction mixture under a pressure of 20 mbar. The oily residue remaining was dissolved in hot ethanol. Cooling this solution to room temperature gave 40 g (75 percent of theory) of 1,3-bis-(4-benzoyl-3-hydroxyphenoxy)-prop-2-yl acrylate in the form of colorless crystals having a melting point of 98° to 100° C. and a purity of 99 percent (HPLC). The UV spectrum gave two absorption maxima at wave lengths of 287 nm (extinction 0.520; extinction coefficient 28,100) and 324 nm (extinction 0.335; extinction coefficient 18,100).

EXAMPLE 2

97 g (0.2 mole) of 1,3-bis-(4-benzoyl-3-hydroxyphenoxy)-2-propanol were esterified analogously to Example 1 with 103 g (1.2 moles) of methacrylic acid. Crystallization from ethanol gave 86 g (78 percent of theory) of 1,3-bis-(4-benzoyl-3-hydroxyphenoxy)-prop-2-yl methacrylate in the form of colorless crystals having a melting point of 138° to 139° C. and a purity of 99 percent (HPLC). The UV spectrum gave two absorption maxima at wave lengths of 287 nm (extinction 0.517; extinction coefficient 28,570) and 324 nm (extinction 0.333; extinction coefficient 18,400).

EXAMPLE 3

(a) 3 g of trifluoromethanesulfonic acid were added to a solution of 48.5 g (0.1 mole) of 1,3-bis-(4-benzoyl-3-hydroxyphenoxy)-2-propanol and 51 g (0.6 mole) of cyanoacetic acid in 750 ml of 1,2-dichloroethane, and the solution was heated for 9 hours at a temperature of 80° to 85° C. After cooling to room temperature, the reaction mixture was washed with three times 400 ml of water. The 1,2-dichloroethane was distilled off from the reaction mixture under a pressure of 50 mbar and a temperature of 35° to 45° C. The residue remaining was recrystallized from acetonitrile. After drying, 48 g (87 percent of theory) of 1,3-bis-(4-benzoyl-3-hydroxyphenoxy)-prop-2-yl cyanoacetate were obtained in the form of slightly yellow, fine crystals having a melting point of 167° to 168° C. and a purity of 99 percent (HPLC).

(b) 1 g of trifluoromethanesulfonic acid was added to a solution of 55.2 g (0.1 mole) of 1,3-bis-(4-benzoyl-3-hydroxyphenoxy)-prop-2-yl cyanoacetate in 300 ml of acetone, and the solution was heated for 3 hours at a temperature of 56° C. After cooling to room temperature, the resulting crystalline precipitate was filtered off with suction and recrystallized from acetone. After drying, 51 g (86 percent of theory) of 1,3-bis-(4-benzoyl-3-hydroxyphenoxy)-prop-2-yl 2-cyano-3,3-dimethylacrylate were obtained in the form of colorless crystals having a melting point of 145° to 147° C. and a purity of 99 percent (HPLC). The structure of the compound obtained was confirmed by UV, IR and NMR spectra.

EXAMPLE 4

97 g (0.2 mole) of 1,3-bis-(4-benzoyl-3-hydroxyphenoxy)-2-propanol were esterified analogously to Example 1 with 120 g (1.2 moles) of 3,3-dimethylacrylic acid. After crystallization from acetone 86 g (76 percent of theory) of 1,3-bis-(4-benzoyl-3-hydroxyphenoxy)- prop-2-yl 3,3-dimethylacrylate were obtained in the form of slightly yellow, fine crystals having a melting point of 148° to 150° C. and a purity of 99 percent (HPLC). The structure of the compound obtained was confirmed by UV, IR and NMR spectra.

EXAMPLE 5

97 g (0.2 mole) of 1,3-bis-(4-benzoyl-3-hydroxyphenoxy)-2-propanol were esterified analogously to Example 1 with 103 g (1.2 moles) of crotonic acid. After crystallization from an acetone/ethanol mixture (ratio by volume 1:2), 83 g (75 percent of theory) of 1,3-bis-(4-benzoyl-3-hydroxyphenoxy)-prop-2-yl crotonate were obtained in the form of fine white crystals having a melting point of 99° to 103° C. and a purity of 99 percent (HPLC). The structure of the compound obtained was confirmed by UV, IR and NMR spectra.

EXAMPLE 6

A solution of 110 g (0.2 mole) of 1,3-bis-(4-benzoyl-3-hydroxyphenoxy)-prop-2-yl methacrylate in 1.2 liters of acetone containing 1.5 g of 50 percent strength benzoyl peroxide (aqueous) was heated under reflux for 16 hours under an atmosphere of nitrogen. After the reaction mixture had cooled to room temperature, the solid reaction product was separated off, washed with twice 500 ml of acetone and dried at a temperature of 60° C. in a circulating air drying cabinet. The dried product was a solid, glass-like mass which, after being ground to a slightly yellow powder, had a glass transition temperature of 107° C. The yield was 105.9 g (96 percent of theory). The residual monomer content was less than 0.01 percent. The UV spectrum gave two absorption maxima at wave lengths of 287 nm (extinction 0.523) and 324 nm (extinction 0.330).

EXAMPLE 7

107.7 g (0.2 mole) of 1,3-bis-(4-benzoyl-3-hydroxyphenoxy)prop-2-yl acrylate in 0.8 liters of acetone were treated analogously to Example 6. Working up the reaction product similarly gave 97.3 g (91 percent of theory) of a slightly yellow powder having a glass transition temperature of 88° C. The residual monomer content was less than 0.01 percent. The UV spectrum gave two absorption maxima at wave lengths of 287 nm (extinction 0.523) and 324 nm (extinction 0.330).

EXAMPLE 8

0.5 g of 50 percent strength benzoyl peroxide (aqueous) was added to a mixture of 0.6 g of 1,3-bis-(4-benzoyl-3-hydroxyphenoxy)-prop-2-yl methacrylate and 20 g of methylmethacrylate, and the mixture was heated in a glass vessel at a temperature of 70° C. for 8 hours under an atmosphere of nitrogen. This gave a solid, transparent block of polymer. The IR spectrum gave a band characteristic for 1,3-bis-(4-benzoyl-3-hydroxyphenoxy)-prop-2-yl methacrylate at a wave number of 1,620 cm$^{-1}$. The appearance, transparency, strength and resistance to chemicals were those of polymethacrylate.

USE EXAMPLE

A commercial color print (format 18 cm×24 cm), which had a gray wedge and a color gradation, was coated with a commercial acrylic lacquer containng 1,3-bis-(4-benzoyl-3-hydroxyphenoxy)-prop-2-yl methacrylate according to Example 2 (sample a). The color print thus treated was irradiated for 2,000 hours with a commercial UV light, at a distance of 50 cm.

For comparison, an untreated color print (sample b) and a color print which had been treated with a commercial acrylic lacquer (sample c) were subjected to the same irradiation. The reference used was an untreated color print which had been stored in the dark (sample d).

Evaluation after the irradiation gave the following results;

Sample a: no fading of color and no graying of the white shades;

Sample b: very severe color fading and very severe graying of white shades;

Sample c: very severe color fading and very severe graying of white shades;

Sample d: no color fading and no graying of white shades.

We claim:

1. An ester formed from 1,3-bis-(4-benzoyl-3-hydroxyphenoxy)-2-propanol and an unsaturated carboxylic acid.

2. An ester as claimed in claim 1, wherein the carboxylic acid is a monocarboxylic acid.

3. An ester as claimed in claim 1, wherein the carboxylic acid is a compound of the formula (2)

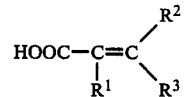

in which $R^1$ denotes a hydrogen atom, a phenyl radical, an alkyl radical having 1 to 12 carbon atoms or a cyano group and $R^2$ and $R^3$ independently of one another denote a hydrogen atom, an alkyl radical having 1 to 8 carbon atoms or a phenyl radical which may be substituted by a lower alkyl or alkoxy radical, or together denote an alkylene radical having 4 or 5 carbon atoms.

4. A stabilizer composition against the effects of UV light, which contains, as the active compound, an ester as claimed in claim 1.

5. A method of stabilizing a plastic against the effects of UV light, which comprises incorporating an ester as claimed in claim 1 into said plastic.

6. A method of preparing homopolymers and copolymers, which comprises polymerizing an ester as claimed in claim 1 under conditions known per se.

7. A polymer composed of or containing recurring units derived from an ester formed from 1,3-bis-(4-benzoyl-3-hydroxyphenoxy)-2-propanol and an unsaturated carboxylic acid.

* * * * *